United States Patent [19]

Rothgery et al.

[11] Patent Number: 5,424,449

[45] Date of Patent: Jun. 13, 1995

[54] PROCESS FOR THE PREPARATION OF 5-AMINOTETRAZOLE

[75] Inventors: Eugene F. Rothgery, North Branford; Karl O. Knollmueller, Hamden, both of Conn.

[73] Assignee: Olin Corporation, Cheshire, Conn.

[21] Appl. No.: 330,881

[22] Filed: Oct. 28, 1994

[51] Int. Cl.$^6$ .............................................. C07D 257/06
[52] U.S. Cl. .................................................. 548/251
[58] Field of Search ........................................ 548/251

[56] References Cited

PUBLICATIONS

J. Thiele, Ann. 270 2(1892), pp. 1–63.
A. Hantzsch and A. Vagt, Ann. 314 1(1901), pp. 339–368.
Stolle, Ber. 62B 7 (1929), pp. 1118–1125.
J. S. Mihina and R. M. Herbst, J. Org. Chem., 155 (1950), pp. 1028–1092.

*Primary Examiner*—David B. Springer
*Attorney, Agent, or Firm*—Dale L. Carlson

[57] ABSTRACT

The compound 5-aminotetrazole is prepared by a process which comprises (a) reacting a hydrazine salt of a mineral acid with cyanamide to form the corresponding aminoguanidine salt, (b) diazotizing the aminoguanidine salt to the corresponding guanylazide salt, and (c) cyclizing the guanylazide salt to 5-aminotetrazole.

29 Claims, No Drawings

PROCESS FOR THE PREPARATION OF 5-AMINOTETRAZOLE

BACKGROUND OF THE INVENTION

This invention relates to the production of 5-aminotetrazole. More particularly, the invention relates to improvements in making this valuable chemical, including a one-pot process for the commercial manufacture of 5-aminotetrazole economically and in improved quality and yield.

The compound 5-aminotetrazole, hereinafter alternatively referred to by the abbreviated name "5-ATZ" is a well-known chemical intermediate which is also used in making propellants. In recent years, it has been found of utility in an increasing number of non-military applications including for example the production of automotive air bags.

However, only limited information has been published in the technical literature on methods of synthesizing 5-ATZ. Briefly, according to the prior art dating back to 1901, 5-ATZ can be synthesized by one of two routes which are described in two old German publications. The first involves the diazotization of aminoguanidinium nitrate with sodium nitrite and nitric acid to form a guanylazide salt intermediate which is then cyclized by heating in the presence of sodium acetate to 5-aminotetrazole. See Thiele, Ann. 270, 54 (1892).

The second method, according to the prior art, for producing 5-ATZ reacts hydrazoic acid, derived from sodium azide and an acid, with cyanamide or dicyandiamide. See Hantsch and Vogt, Ann. 314, 339 (1901).

These prior art methods are not well suited for the efficient, economically feasible production of 5-ATZ on an commercial scale. Moreover, the product of the first method typically is plagued with objectionable yellowish discoloration, the removal of which would add substantially to the cost of manufacture of 5-aminotetrazole.

BRIEF SUMMARY OF THE INVENTION

Now an improved process has been developed for the manufacture of 5-ATZ in high yield and purity. Moreover, the process of the invention is particularly adapted for use as a an economically feasible route for the production of 5-ATZ on a commercial scale.

In accordance with the invention, 5-ATZ which is substantially free of discoloration is prepared by a process which comprises
  (a) reacting an aminoguanidine salt with a diazotization agent to form the corresponding guanylazide salt, the diazotization agent being selected from (i) nitrous acid which is produced in situ under controlled conditions and (ii) an alkyl nitrite; and (b) cyclizing the guanylazide salt to 5-aminotetrazole.

Pursuant to another embodiment of the invention, an improved process is provided for the production of 5-ATZ, which process is particularly adapted for use as a one pot process and comprises
  (1) reacting together cyanamide with a hydrazine salt, i.e., the product of the reaction of hydrazine with a mineral acid, to form the corresponding salt of aminoguanidine;
  (2) diazotizing the aminoguanidine salt to the corresponding guanylazide salt; and
  (3) cyclizing the guanylazide salt to 5-aminotetrazole.

Further according to the invention, improvements and refinements are provided which can be used in any process that employs the sequence of steps summarized above, to produce pure 5-ATZ economically and in high yields.

DETAILED DESCRIPTION OF THE INVENTION

As noted above, the production of 5-ATZ is achieved by the reaction of an aminoguanidine salt with a diazotization agent to form the corresponding guanylazide salt, which is then cyclized to 5-ATZ. The aminoguanidine salt may be obtained from any suitable source or synthesized by an suitable method. In accordance with the preferred embodiments of the invention, it is prepared by reacting the corresponding hydrazine salt with cyanamide, the former being the product of the reaction of hydrazine with a mineral acid. All of these reaction steps, which are preferably carried in an aqueous medium, are described in more detail below.

As used in preparing the hydrazine salt, the hydrazine can be hydrous or anhydrous. However, for reasons of economy and practicality, it is preferable to employ an aqueous solution of hydrazine in any suitable concentration, such as from about 20 to about 70, and preferably about 30 to about 64, percent by weight. As for the acid, this can be any suitable mineral acid. Illustrative are hydrochloric, hydrobromic, nitric and sulfuric acids, the corresponding hydrazine salts of which being hydrazinium chloride, bromide, nitrate and sulfate, respectively. The preferred acids are hydrochloric, hydrobromic and nitric acids, with hydrochloric acid being most preferred. As is the case with the hydrazine, the concentration of the mineral acid may varied over a reasonably wide range. Typically, commercially available concentrations may be used as such or they may be diluted with water to any suitable concentration. For practical reasons, the acid concentration preferably should not be below about 20 percent by weight such as from about 25 to about 35, and more preferably about 28 to about 32, percent by weight.

In accordance with the practical embodiments of the invention, the concentrations of the hydrazine solution and the acid solution should be selected such that the resulting hydrazine salt solution would have a concentration from about 30 to about 40, and more preferably from about 32 to about 36 percent by weight.

In preparing the hydrazine salt, any suitable molar proportion of mineral acid may be employed per mole of hydrazine. As a practical matter, however, since the reaction involves equi-molar proportions of the two starting materials, it is preferable to use from about 0.80 to about 1.05 moles of acid per mole of hydrazine. In accordance with a particularly preferred embodiment of the invention, no more than one mole of the acid, such as from about 0.85 to about 0.98, and still more preferably about 0.92–0.97 mole, is used per mole of hydrazine. This is based on the discovery that when the hydrazine salt is reacted with the cyanamide, the reaction proceeds faster and with maximum conversion to the corresponding aminoguanidine salt when a small excess of free hydrazine is present. Thus in accordance with this preferred embodiment, the reaction of the hydrazine salt with the cyanamide is effected in the presence of a small amount of free hydrazine, and one convenient expedient to achieve this is to use, when preparing the hydrazine salt, an excess of hydrazine over the stoichiometric amount required for reaction with the acid. Usually a small, fractional excess is sufficient to achieve the desired objective.

The reaction of hydrazine with the mineral acid can proceed at any suitable temperature, such as from 0° to about 100° C. However, inasmuch as the reaction is exothermic, to avoid excessive heat which may lead to loss of some hydrazine, some cooling may be necessary or desirable such as to maintain a reaction temperature no higher than about 60° C., such as from about 10° to about 50° C. and more preferably about 20°–40° C. Any suitable conventional means may be employed to effect the cooling.

The cyanamide, preferably in aqueous solution of any suitable concentration such as from about 40 to about 60, preferably about 45 to about 55, percent by weight (the commercially available 50% concentration being most preferred), is added to and reacted with the hydrazine salt in any suitable relative molar proportion. Inasmuch as the stoichiometry of the reaction requires equimolar proportions of the two reactants, ordinarily a range of from about 0.8 to about to about 1.2 moles of cyanamide are used per mole of hydrazine salt. In accordance with the preferred embodiments, the proportion of cyanamide used is determined relative to the total hydrazine present, i.e., free hydrazine as well as hydrazine salt; and per each mole of total hydrazine, cyanamide is used in a proportion ranging from about 0.88 to about 1.12, more preferably about 0.95–1.05, moles per mole of total hydrazine.

In carrying out the aminoguanidine salt-forming reaction, elevated temperatures above about 40° C. are employed, such as from about 50° to about 100°, preferably about 70°–90° C. and more preferably about 82°–88° C. Procedurally, the reaction may be effected for example by first heating the hydrazine salt solution to a temperature within the desired range and then adding the cyanamide, the desired temperature being maintained until the reaction is completed. If the hydrazine salt is the hydrochloride, the reaction can be illustrated by equation I as follows:

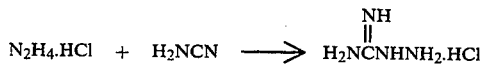

$$N_2H_4 \cdot HCl + H_2NCN \longrightarrow H_2NC(NH)NHNH_2 \cdot HCl \qquad I$$

The product of the reaction, comprised mainly of an aqueous solution of the aminoguanidine salt, is next reacted with a diazotization agent to form the corresponding guanylazide salt. The preferred diazotization agents in accordance with the invention are nitrous acid and the alkyl nitrites. The use of the latter is preferred when the process of the invention is implemented using a multi-reactor system, which would be particularly suited for a continuous process operation; for it has been found that nitrosating the aminoguanidine salt with an alkyl nitrite has the desirable result of yielding a final 5-ATZ product which is exceptionally clean and substantially free of discoloration. On the other hand, the use of nitrous acid, in accordance with another preferred embodiment of the invention, carries the advantage of not requiring a separate reaction vessel for generating this diazotization agent. As such, the use of nitrous acid would be particularly suited, though not limited, to single-reactor operation or one-pot processes for making 5-ATZ.

The nitrous acid is generated in situ by conventional methods such as by the reaction of an acid with a nitrite salt. Any suitable acid and nitrite salt may be used. Illustrative acids are the mineral acids including, for example, hydrochloric, hydrobromic, nitric and sulfuric acids; and illustrative nitrite salts include the alkali metal and alkaline earth metal nitrites, the alkali metal nitrites, such as sodium and potassium nitrite, being preferred. For reasons of economy and practicality, it is particularly preferred to react hydrochloric acid with sodium nitrite, usually in aqueous solution, to generate the nitrous acid. Any suitable relative molar proportions of acid and nitrite may be used, but in actual practice approximately equi-molar amounts are employed; and although there is not a specific temperature or range of temperatures that the reaction will proceed at, it is preferable to effect the reaction at a temperature from about 10° C. to about 30° C., more preferably about 15° C. to about 25° C., in order to substantially avoid the occurrence of any side reactions. Since the reaction is exothermic, cooling may be required for controlling the temperature within these preferred ranges, and any conventional cooling means may be used for this purpose.

In effecting the in situ generation of nitrous acid, it is preferable to first add the mineral acid to the aqueous aminoguanidine salt solution, followed by the gradual addition of the nitrite salt. In accordance with the invention, it is particularly advantageous to control the rate of addition of the nitrite salt such as to substantially preclude the presence of free or excess nitrite ions in the solution. That is to say, the rate of nitrite addition should preferably be so gradual or regulated as to insure substantially complete consumption or reaction of the nitrous acid, as it is formed, with the aminoguanidine salt. This preferred procedure is important in view of the discovery, according to the invention, that minimizing or precluding the presence of unreacted nitrous acid has a direct beneficial effect on the purity or reduction of discoloration of the final 5-ATZ product. Any suitable conventional method may be used to monitor the solution in order to implement this preferred procedure, such as by using iodide oxidation to iodine on a spot plate. It may also be desirable in certain instances to effect the in situ generation of nitrous acid in the presence of an alcohol, e.g., ethanol, which serves as a modifier.

The diazotization reaction can be represented by the following equation where the aminoguanidine salt is aminoguanidinium chloride:

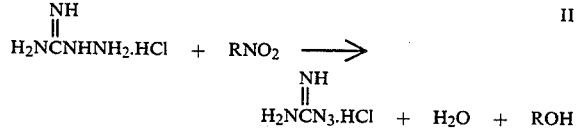

$$H_2NC(NH)NHNH_2 \cdot HCl + RNO_2 \longrightarrow H_2NCN_3 \cdot HCl + H_2O + ROH \qquad II$$

in which R is hydrogen or an alkyl group. Thus when nitrous acid is used as the diazotization agent (R=H), water (2 moles) would be a by-product; whereas, if an alkyl nitrite is used (R=alkyl), the by-products are one mole of water and one mole of alcohol.

With respect to the alternative alkyl nitrite diazotization agent which is used according to the invention, this can be any suitable such nitrite. Generally, the alkyl nitrite may be represented by the formula RNO, in which R is alkyl, generally having no more than 8, and preferably no more than 6, carbon atoms such as methyl, ethyl, propyl, butyl, pentyl, and hexyl. Particularly preferred are alkyl nitrites having up to 4 carbon atoms, with methyl and ethyl nitrites being most preferred.

The alkyl nitrite can be obtained from any suitable source or prepared by any suitable method. Conveniently, it is produced by the reaction, preferably in a separate reactor, of an alcohol with a nitrite salt in the presence of a mineral acid, and then it is added to the aminoguanidine salt solution. The alcohol can be a primary, secondary or tertiary alcohol, and the nitrite salt can any suitable such salt, of which the alkali metal nitrites are illustrative. Further details concerning the preparation of alkyl nitrites can be found for example in U.S. Pat. No. 2,615,896 and in Cole, Organic Syntheses, Vol. 2 (1943), P. 204, both of which are incorporated by reference herein. Advantageously, an alcohol having from 1 to 6 carbon atoms is reacted with an alkali metal nitrite, e.g., sodium nitrite, using from about 0.8 to about 2.0 moles of alcohol per mole of nitrite, the reaction being effected with the addition of a suitable mineral acid.

To the extent that the lower alkyl nitrites are either gases or low boiling liquids, they are preferably bubbled into the aminoguanidine salt solution; whereas, this precaution is ordinarily unnecessary when using a more stable, liquid higher alkyl nitrite.

When an alkyl nitrite is used as the diazotization agent, it has been found that the diazotization reaction proceeds more readily in the presence of an acidic medium. Accordingly, the addition of an acid, e.g., a mineral acid, prior to or after commencement of the diazotization reaction is recommended, the proportion of such acid addition to be determined by routine experimentation on a case-by-case basis.

The diazotization reaction is carried out at any suitable temperature. Typically, a temperature below about 60° C. is employed such as from about 0° to about 50° C., preferably from about 8° to about 30° C. and more preferably about 12°–20° C.

Following the diazotization of the aminoguanidine salt to the corresponding guanylazide salt, the latter is cyclized to form 5-aminotetrazole as illustrated in equation III below in which the cyclization is effected in the presence of ammonia:

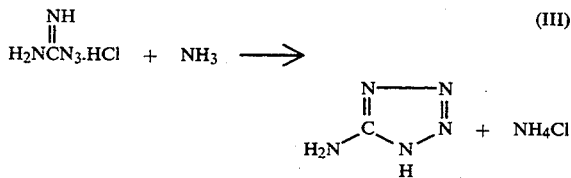

The cyclization step is achieved at elevated temperatures and by raising the pH of the guanylazide salt solution by means of a base. For this purpose, any one of a wide variety of suitable alkaline materials may be used including, for example, ammonia, a hydroxide, acetate or carbonate of an alkali metal or an alkaline earth metal. The preferred bases are ammonia and sodium or potassium hydroxide, acetate or carbonate, with ammonia being most preferred.

Such a proportion of base is used as to raise the pH of the guanylazide solution to at least about 4, such as from about 4 to about 6.5 and preferably from about 4.2 to about 6.0. A most preferred pH range of from about 4.5 to about 5.8 is recommended to achieve an optimum rate of conversion to 5-ATZ. The exact amount of base which is required can be determined by routine experimentation depending on the particular base which is used and the desired pH. Thus for example, to achieve a pH of about 5.5 using ammonia, approximately 1.3 moles of the ammonia would be required per mole of guanylazide salt.

As indicated earlier, the cyclization step is effected at elevated temperatures, for example above about 40° C., such as from about 50° to about 125° C., preferably about 80°–110° C. and more preferably about 95°–105° C.

The product of the cyclization reaction typically comprises an aqueous solution of 5-ATZ and by-product salt, e.g., ammonium chloride when ammonia is used as the base. Isolation and recovery of the 5-ATZ can be achieved by any suitable or conventional means. Ordinarily, precipitation of the 5-ATZ can be brought about by cooling the reaction product mixture to about 55° C. or lower. However, it has been found that at a pH in excess of about 5, the precipitation of the 5-ATZ is not complete, i.e., some of the 5-ATZ in the form of the salt thereof remains dissolved. On the other hand, at a pH below 3.0 the amphoteric 5-ATZ would form more salt with the strong acid present. Accordingly, to optimize the isolation and recovery of the product according to the invention, it is preferable to adjust and maintain the pH at from about 3.5 to about 4.5. It is also preferable to effect the cooling of the reaction product mixture gradually in order to avoid very sudden and fast precipitation of 5-ATZ, and thereby minimize the presence of impurities in the product.

The precipitated product of the process of the invention is a whitish, crystalline 5-aminotetrazole monohydrate, which is fairly pure and substantially free of discoloration. As such, no costly or burdensome operations are necessary to purify it or to improve it appearance. If desired, the water of hydration can be easily removed by heating for several hours to a temperature above about 100° C.

As noted earlier, in accordance with a preferred embodiment of the invention, a one-pot process is provided for the efficient and economical. production of high quality 5-ATZ. As used throughout the specification and claims herein, the term "one-pot process" is intended to mean any process, the series of reactions or steps of which are carried out using substantially one reaction medium or vessel, as opposed to two or more distinct or individual reactors. The resulting economies are quite substantial, particularly in a commercial-scale operation.

The one-pot process of the invention comprises the following steps:
(a) placing and reacting together, in a reaction vessel, cyanamide and a hydrazine salt of a mineral acid to form the corresponding aminoguanidine salt;
(b) generating nitrous acid in the reaction vessel and effecting the diazotization of the aminoguanidine salt to the corresponding guanylazide salt; and
(c) adding to the reaction vessel a sufficient proportion of a base to achieve a pH of from about 4 to about 6.5 and effecting the cyclization of the guanylazide salt to 5-aminotetrazole.

In accordance with the most preferred embodiments, the one-pot process of the invention begins with the preparation of the hydrazine salt in the same reaction vessel, to which the cyanamide is then added to produce the aminoguanidine salt intermediate. As such, the process can be described as being comprised of the following steps:

(a) placing and reacting together, in a reaction vessel, hydrazine and a mineral acid to form the corresponding hydrazine salt of said acid;
(b) adding to the reaction vessel an aqueous solution of cyanamide and reacting this with the hydrazine salt to form the corresponding aminoguanidine salt;
(c) generating nitrous acid in the reaction vessel and effecting the diazotization of the aminoguanidine salt to the corresponding guanylazide salt; and
(d) adding to the reaction vessel a sufficient proportion of a base to achieve a pH of form about 4.2 to about 6.0 and effecting the cyclization of the guanylazide salt to 5-aminotetrazole.

The following examples are provided to illustrate the invention. In these examples, the main reaction vessel used is a one liter or three hundred milliliter, three-neck flask equipped with a stirrer, a thermometer with a thermocontroller attached thereto, an adapter for holding a reflux condenser, and a drop-in funnel having a side arm for admitting nitrogen to blanket the reactants. Also provisions are made for cooling the flask by means of a water or ice bath and for heating the flask by means of a heating mantle connected to the thermocontoller. All parts and percentages in the examples are by weight unless otherwise specified.

Example 1

Into the one-liter flask, there were charged 50.06 g of hydrazine hydrate (64.2% $N_2H_4$-content) or 1 mole and 85 g water for dilution. While cooling with ice, 112 g of 32.0% hydrochloric acid (0.98 mole) was added dropwise. When the addition was completed the solution was heated to 85° C. Through a dropping funnel 84.5 g of a 50% cyanamide solution was added. The first 20% was added quickly. The temperature began to rise to 90° C. and was maintained during further addition of the cyanamide between 85 and 95° C. During the addition, lasting 20 minutes, no external heating was necessary. When, after the cyanamide addition, the temperature began to drop, heat was applied; the thermostat was set at 85° C. and the heating continued for 2 hrs.

Titration of a 855.1 mg sample with 0.1N NaOH between pH 3.8 and 9.3 consumed 1.35 ml of 0.1002N NaOH, which; indicated a 94.7% conversion. The pH of the original sample was 7.4, adjusted to 3.8 with a few drops 0.1N HCl.

The reactor contents were now cooled to 25° C. and 114 g of 32% HCl (1 mole) added. While maintaining the temperature between 17° and 22° C. and stirring vigorously a solution of 71.2 g $NaNO_2$ (assay 97%) 1 mole in 152 g water was added dropwise. Only a trace of NO was seen. After the addition the contents were held at about 20° C. for 20 minutes. To the reactants were added rapidly 110.2 g ammonia solution, containing 20.32% $NH_3$. (1.32 moles). The contents were heated to beginning reflux and held there for 2 hrs.

The pH of the mixture was 5.5–5.6 (measured on small samples diluted 1:1 with water). HCl was now added incrementally until the pH was 4 to 4.1. A total of 38.9 g (32%) HCl was required (0.34 Moles).

Upon cooling the 5-ATZ began crystallizing at about 54° C. The contents were slowly cooled to 10° C. By means of a filter stick the supernatant solution was removed as much as possible. The filtrate weighed 603 g. To remove chloride, 240 g of water were added, the contents stirred and heated briefly to 45° C., followed by cooling to 10° C. The contents were transferred to a Buechner funnel and washed three times with about equal portions of water, giving 767 g combined wash water (from slurry and washes). The filter cake was dried for 3 hrs at 110° C. producing 63.9 g anhydrous 5-ATZ or 74.8%. (Assay by titration 99.8 and 100.2%).

Examples 2–8

In these examples, the same procedure of Example 1 were followed using a 300-ml flask. The HCl concentration used throughout is 32.23%. Amounts of reactants, other variables and the results of these examples are summarized in the Table below, in which the details are reported in reference to the four reaction steps, namely, step 1: the reaction of hydrazine with hydrochloric acid to form hydrazinium chloride followed by the reaction of the latter with cyanamide to form aminoguanidinium chloride, step 2: the diazotization of the aminoguanidinium chloride to guanylazidium chloride, and step 3: the cyclization of guanylazidium chloride to 5-ATZ.

TABLE

5-ATZ Synthesis Data

| | Step 1 | | | | Step 2 | | |
|---|---|---|---|---|---|---|---|
| Examp. No. | N2H4 64.20% | HCl 32.23% | Water Grams | H2N-CN 50% | HCl 32.23% | NaNO2 Grams | H2O Dilut |
| 2 | 15.20 | 33.50 | 32.73 | 25.55 | 33.80 | 21.56 | 58.80 |
| 3 | 15.20 | 33.50 | 25.00 | 25.55 | 38.19 | 21.56 | 58.80 |
| 4 | 15.10 | 33.60 | 21.57 | 25.50 | 38.55 | 21.52 | 50.14 |
| 5 | 15.10 | 33.60 | 17.45 | 25.44 | 33.60 | 21.49 | 50.00 |
| 6 | 15.00 | 33.54 | 12.40 | 25.23 | 33.54 | 21.30 | 45.00 |
| 7 | 13.60 | 33.54 | 13.60 | 26.73 | 33.54 | 21.40 | 45.00 |
| 8 | 15.00 | 33.54 | 12.40 | 25.23 | 33.54 | 21.30 | 45.00 |

| | Step 3 | | | Weights & Yields | | |
|---|---|---|---|---|---|---|
| Examp. No | NH3 20.32% | HCl 32.23% | Extra Water | Filtrate grams | Yield grams | Yield % |
| 2 | 29.50 | 8.77 | | 197.70 | 18.60 | 72.00 |
| 3 | 28.00 | 0.00 | 82.00 | 255.90 | 16.70 | 64.60 |
| 4 | 28.95 | 0.00 | 80.00 | 236.40 | 17.26 | 66.90 |
| 5 | 26.80 | 0.00 | 152.00 | 222.84 | 18.53 | 72.60 |
| 6 | 28.14 | 6.20 | 0.00 | 198.50 | 17.53 | 68.90 |
| 7 | 24.00* | 2.00 | 40.00 | Not Weighed | 7.70 | 33.50 |
| 8 | 28.14 | 6.08 | 80.00 | Not Weighed | 17.53 | 68.70 |

*Instead of ammonia, 24.00 g of 20.32% sodium hydroxide solution was used.

Example 9

This experiment was conducted in the presence of ethanol to serve as a modifier during the diazotation step. Following the procedures described above aminoguanidine hydrochloride intermediate was prepared from 14.93 g hydrazine hydrate (64.4% 0,3 mole 0, diluted with 30 ml water, 33.4 g of 31.72% HCl (0.294 mole) and 25.23 g of 50% cyanamide (0.3 mole).

To the cooled solution was added 34.09 g of 31.72% HCl (0.3 mold) and 14 g ethanol (0.3 mole). A solution of 21.34 g NaNO$_2$ (0.3 mole) in 50 ml water was added through the dropping funnel.

After the addition the ring closure was accomplished by adding 31.4 g of a 22.1% ammonia solution (0.41 mole ammonia) and refluxing for 2 hrs.

After adjustment to pH 4 and isolating the 5-ATZ in the usual way we obtained 17.5 g anhydrous material (68.6% yield). The product was free of discoloration.

Example 10

Example 9 was repeated with the same amount of ingredients, but instead of ethanol, 13.9 g of methanol were used. The product was 17.7 g of 5-ATZ (69,4% yield) which was white and free of discoloration.

Example 11

This example is provided to demonstrate a continuous reaction simulation, although only one reactor was used here rather multiple reactors. However each step was carried out for about the same length of time. In this instance a holding time of 2 hours was arbitrarily selected for each step.

Simulation Reactor 1

Into the one-liter flask was charged. 50.06 g of 64.4% hydrazine (1.002 Moles) and 85 grams waters.

With cooling a solution of 112 g of 32% hydrochloric acid (0.983 moles) was added. Towards the end of the addition the temperature was allowed to rise to 40° C. After the hydrochloric acid addition was completed the ice bath was replaced by a heater attached to a thermoregulator. The dropping funnel was now charged with 85 g of 50% cyanamide solution (1.01 mole). When the temperature reached 80° C. the addition of cyanamide was started. After a brief induction period the temperature rose above the set point of the heater and was maintained around 85°–90° C. After the addition was completed, the temperature began to fall and was now maintained at 85° C. for 2 hrs.

In timing this reaction it is assumed that the neutralization of hydrazine with hydrochloric acid can be achieved fairly easily on a continuous basis in a plant by metering the components in the right proportions through a small mixing chamber. We therefore did not time the neutralization step. A larger supply of hydrazine hydrochloride could also be kept on hand.

Simulation Reactor 2

The reactants were cooled to 20° C. while 114 g 32% hydrochloric acid (1 mole) was added. The dropping funnel was charged with a solution of 71.2 g sodium nitrite (97% assay, 1 mole) in 150 g water. The sodium nitrite was added during 1.45 hrs while the temperature was maintained at 20°±4° C. The mixture was held for 15 minutes more giving a 2 hr reaction time.

Simulation Reactor 3

To the contents of the previous step was added rapidly 108 g of ammonia solution, containing 22.1% as NH$_3$ (1.4 moles). The pH was 5.7. Full heat to reflux (104° C.) was applied for 2 hrs. After this time the heat was removed. We added 46 g 32% hydrochloric acid (0.4 moles) and allowed the solution now at a pH of 3.9 to cool slowly. Simulation of Crystallizer or Holding Tank Large crystals separated on slow cooling for 1.5 hrs. The crystals were filtered on a Buechner funnel. The filtrate weighed 714 g and had a pH of 5.3 after removal of product.

The product was slurried three times with water on the funnel and filtered. The combined wash waters from the washing was 503 go The product was dried at 110° C. for 3 hrs giving 59.7 g anhydrous 5-ATZ. The yield was 70%. The product was slightly off white.

Example 12

In this example the amount of sodium nitrite was controlled to insure complete reaction of the nitrous acid as it is formed and avoid the presence of free nitrite ions. As is shown, the observance of this precaution results in a 5-ATZ final product which is free of discoloration.

The experimental conditions and amounts of reagents used were the same as in Example 10 except that no alcohol was used here.

During the nitrosation step we began testing for free nitrous acid when about 80% of the sodium nitrite solution had been added. The test involved adding a drop reactor content to a few drops potassium iodide/starch solution on a spot plate. At the moment free nitrous acid was present iodine was liberated in the test well. At the same time the solution became slightly yellow. Without a waiting period the cyclization was initiated by addition of ammonia, followed by the usual isolation procedure.

The amount of unused sodium nitrite was determined by weighing back the contents of the dropping funnel. In this run 0.29 mole sodium nitrite was consumed. After the usual workup we obtained 17.8 g clean 5-ATZ (69.8% yield) which was free of discoloration.

Example 13

Into the three-neck flask reactor there were charged 15.1 g of 64% hydrazine (0.303 mole) followed by 33.5 g of 32% HCl (0.294 mole). After heating the contents to 85° C., 25.5 g of a 50% aqueous solution of cyanamide (0.304 mole) was added slowly over a period of about 15 minutes. After the exotherm, the reaction mixture was heated for two hours at 85° C. The resulting solution had a pH of 7.4. Titration of a sample at an adjusted pH between 3.7 and 9.2 revealed a 94.7% conversion to aminoguanidine hydrochloride.

An ethyl nitrite generator was set up which consisted of a 250 ml Erlenmeyer flask charged with 21.56 g of sodium nitrite (97% assay), slurried in 30 ml of water and 15 g of 98% technical ethanol. An equaliberated dropping funnel with an off-gas tube was charged with 15 g of 98% sulfuric acid in 30 ml of water. A teflon tubing was attached to the exit tube of the dropping funnel leading into the main reactor in such a way that the inlet was under the surface of the aminoguanidine hydrochloride solution. 12.7 g of 32% HCl was poured into the dropping funnel. To monitor the pressure and uptake, an oil bubbler was attached to the reactor.

The generator contents were stirred magnetically on a hot plate in order to keep the contents at about 50° C. The sulfuric acid was added very slowly to the nitrite over a period of 1.5 hours, generating a steady stream of ethyl nitrite. No discoloration was noted during the nitrosation step.

To effect the cyclization of the guanylazide salt, a 22.1% ammonia solution was added incrementally. The pH began to drop after some heating and after about 18.7 g of ammonia had been added. Overall, a total of 38.4 g of the ammonia solution was needed to maintain the pH at 5.5. The reflux boiling point was around 90° C. because of the ethanol generated from the ethyl nitrite. After one hour of reflux a 32% HCl solution was added incrementally to achieve and maintain a pH of 4. On cooling, 5-ATZ hydrate crystallized as a white product and filtered out. After three water washes the filter cake was dehydrated at 110° C. yielding 19.05 g of 73.7% anhydrous 5-ATZ which was white and free of any discoloration.

What is claimed is:

1. A process for producing 5-aminotetrazole which comprises:
   (a) reacting an aminoguanidine salt of a mineral acid with a diazotization agent to form the corresponding guanylazide salt, said diazotization agent being selected from the group consisting of:
      (i) nitrous acid which is produced in situ by the reaction of a mineral acid with a nitrite salt, said reaction being controlled such as to assure consumption of substantially all of the nitrous acid, as it is formed, and thereby substantially preclude the presence of free nitrite ions, and
      (ii) an alkyl nitrite; and
   (b) cyclizing said guanylazide salt to 5-aminotetrazole.

2. The process of claim 1 wherein said aminoguanidine salt is selected from the group consisting of aminoguanidinium chloride, aminoguanidinium bromide and aminoguanidinium nitrate.

3. The process of claim 2 wherein said nitrite salt is an alkali metal nitrite.

4. The process of claim 3 which includes the additional step of isolating and recovering said 5-aminotetrazole.

5. The process of claim 4 wherein said diazotization agent is nitrous acid.

6. The process of claim 5 wherein said mineral acid is hydrochloric acid and said nitrite salt is sodium nitrite.

7. The process of claim 4 wherein said diazotization agent is an alkyl nitrite.

8. The process of claim 7 wherein said alkyl nitrite contains from 1 to 6 carbon atoms.

9. The process of claim 8 wherein said alkyl nitrite is methyl nitrite or ethyl nitrite.

10. A process for making 5-aminotetrazole which comprises:
    (a) reacting a hydrazine salt of a mineral acid with cyanamide in an aqueous medium containing free hydrazine to form the corresponding aminoguanidine salt;
    (b) diazotizing said aminoguanidine salt to the corresponding guanylazide salt; and
    (c) cyclizing said guanylazide salt to 5-aminotetrazole.

11. The process of claim 10 wherein said hydrazine salt is prepared by reacting a mineral acid with hydrazine using at least about one mole of hydrazine per mole of acid.

12. The process of claim 11 wherein said mineral acid is selected from the group consisting of hydrochloric, hydrobromic and nitric acid.

13. The process of claim 12 wherein the diazotization of said aminoguanidine salt is effected by reacting it with a diazotization agent selected from the group consisting of nitrous acid and an alkyl nitrite.

14. The process of claim 13 wherein the preparation of said aminoguanidine salt in step (a) is effected at a temperature from about 70° to about 90° C., the diazotization reaction of step (b) is effected at a temperature from about 8° to about 30° C., and the cyclization of said guanylazide salt is effected at a temperature from about 80° to about 110° C. and a pH from about 4.4 to about 5.8.

15. The process of claim 14 wherein said mineral acid is hydrochloric acid.

16. The process of claim 15 which includes the additional step of isolating and recovering said 5-aminotetrazole.

17. The process of claim 16 wherein said diazotization agent is nitrous acid and this is produced in situ by the reaction of hydrochloric acid with sodium nitrite.

18. The process of claim 17 wherein said diazotization agent is an alkyl nitrite having from 1 to 4 carbon atoms.

19. A one-pot process for the production of 5-aminotetrazole which comprises:
    (a) placing and reacting together, in a reaction vessel, hydrazine and a mineral acid to form the corresponding hydrazine salt;
    (b) adding cyanamide to the reaction vessel and reacting it in an aqueous medium with said hydrazine salt to form the corresponding aminoguanidine salt;
    (c) adding nitrous acid to the reaction vessel and effecting the diazotization of said aminoguanidine salt to the corresponding guanylazide salt; and
    (d) adding to the reaction vessel a sufficient proportion of a base to achieve a reaction mixture pH from about 4 to about 6.5 and cyclizing said guanylazide salt to 5-aminotetrazole.

20. The process of claim 19 wherein said nitrous acid is produced in situ by adding to the reaction vessel an acid and a nitrite salt.

21. The process of claim 20 wherein said mineral acid which is reacted with said hydrazine is selected from the group consisting of hydrochloric, hydrobromic and nitric acid.

22. The process of claim 21 wherein the reaction of step (a) is carried out using at least one mole of said hydrazine per mole of said mineral acid.

23. The process of claim 22 wherein said nitrite salt is an alkali metal nitrite.

24. The process of claim 23 wherein said base is selected from the group consisting of ammonia, an alkali metal hydroxide, an alkali metal acetate and an alkali metal carbonate.

25. The process of claim 24 which includes the additional step of precipitating and recovering said 5-aminotetrazole.

26. The process of claim 25 wherein hydrochloric acid is used as the mineral acid in step (a) and the resulting hydrazine salt is hydrazinium chloride.

27. The process of claim 26 wherein said nitrous acid is produced by the reaction of hydrochloric acid with sodium nitrite.

28. The process of claim 27 wherein the hydrazine salt-forming reaction of step (a) is carried out at a temperature from about 20° to about 40° C. the aminoguanidine salt-forming reaction of step (b) is carried out at a temperature from about 70° to about 90° C., the diazotization of said aminoguanidine salt in step (c) is carried out at a temperature from about 8° to about 30° C., and the cyclization of said guanylazide salt in step (d) is effected at a temperature from about 80° to about 110° C. and a pH from about 4.4 to about 5.8.

29. The process of claim 28 wherein said base is ammonia.

* * * * *